(12) United States Patent
White (10) Patent No.: US 11,708,558 B2
(45) Date of Patent: Jul. 25, 2023

(54) LIQUID SPORULATION METHOD AND SPORULATION BROTH

(71) Applicant: American Sterilizer Company, Mentor, OH (US)

(72) Inventor: Nicholas M. White, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 196 days.

(21) Appl. No.: 16/937,990

(22) Filed: Jul. 24, 2020

(65) Prior Publication Data

US 2021/0024880 A1    Jan. 28, 2021

Related U.S. Application Data

(60) Provisional application No. 62/879,259, filed on Jul. 26, 2019.

(51) Int. Cl.
*C12N 3/00*    (2006.01)

(52) U.S. Cl.
CPC ..................... *C12N 3/00* (2013.01)

(58) Field of Classification Search
CPC .................. C12N 3/00; C12N 1/20
See application file for complete search history.

(56) References Cited

U.S. PATENT DOCUMENTS

| | | | |
|---|---|---|---|
| 2013/0224757 A1 | 8/2013 | Bjoernvad et al. |
| 2014/0099657 A1 | 4/2014 | Buhr |
| 2014/0308733 A1 | 10/2014 | Nishiyama et al. |
| 2018/0044701 A1 | 2/2018 | Mu et al. |
| 2019/0002819 A1 | 1/2019 | Heffron |

FOREIGN PATENT DOCUMENTS

| | | |
|---|---|---|
| CN | 107475172 A | 12/2017 |
| EP | 3282008 A1 | 2/2018 |
| WO | 2008043368 A2 | 4/2008 |
| WO | 2018163094 A1 | 9/2018 |

OTHER PUBLICATIONS

Rowe et al., Journal of Bacteriology, 1975, vol. 124, No. 1, p. 279-28.*
Seale et al., Applied and Environmental Microbiology, 2008, Vo. 74, No. 3, p. 731-737.*
International Preliminary Report on Patentability for related International Application No. PCT/US2020/043421 dated Nov. 12, 2021.
Kathryn L. Nawrocki et al.; "CodY-Dependent Regulation of Sporulation in *Clostridium difficile*", Journal of Bacteriology, vol. 198, No. 15, Aug. 2016, pp. 2113-2130.
Himedi et al.; "Sporulation Broth", Feb. 2015, XP055625581, Retrieved from the Internet: URL:http://himedialabs.com/TD/M1018. pdf [retrieved on Sep. 24, 2019].
Invitation to Pay Additional Fees and partial international search report for corresponding Application No. PCT/US2020/043421 dated Nov. 5, 2020.
Thompson P. J. et al.: "Sporulation of *Bacillus stearothermophilus*", Applied Microbiology, vol. 15, No. 5, Jan. 1, 1967, pp. 975-979.
Luisa F. Posada-Uribe et al.: "Effect of medium components and culture conditions in *Bacillus subtilis* EA-CB0575 spore production", Bioprocess and Biosystems Engineering, vol. 38, No. 10, Oct. 1, 2015, pp. 1879-1888.
Verma Neelam et al.: "Screening of different media for sporulation of *Bacillus megaterium*". International Journal of Microbiology Research and Reviews. vol. 1. No. 4. Apr. 1, 2013, pp. 68-73.
Anonymous: "Difco(TM) Tryptone Peptone. Catalog No. 211921". ThermoFisher Scientific. product catalog. Feb. 15, 2021, pp. 1-1.
PCT/US2020/043421; PCT International Search Report and Written Opinion of the International Searching Authority dated Feb. 24, 2021.

* cited by examiner

*Primary Examiner* — Kade Ariani
(74) *Attorney, Agent, or Firm* — Renner, Otto, Boisselle & Sklar, LLP (57) ABSTRACT

A liquid sporulation method is described. A first liquid culture is prepared by adding bacterial cells to a sporulation broth, wherein an optical density ($OD_{600}$) of the first liquid culture is in a range of 0.001 to 0.01. The first liquid culture is incubated and an optical density ($OD_{600}$) thereof is increased to be in a range of 0.2 to 2.0. Second liquid culture is prepared by adding the incubated first liquid culture to a predetermined amount of additional sporulation broth, wherein an optical density ($OD_{600}$) of the second liquid culture is in the range of 0.001 to 0.1, and a ratio of a volume of the second liquid culture to a volume of the first liquid culture is in a range of 10:1 to 150:1. The second liquid culture is incubated so an optical density ($OD_{600}$) thereof is increased to be in a range of 1.0 to 4.0.

16 Claims, 1 Drawing Sheet

LIQUID SPORULATION METHOD AND SPORULATION BROTH

RELATED APPLICATION DATA

This application claims the benefit of U.S. Provisional Patent Application No. 62/879,259, filed Jul. 26, 2019, the disclosure of which is incorporated herein by reference in its entirety.

TECHNICAL FIELD

The present disclosure relates to a method for producing spores, and more specifically to a liquid sporulation method and sporulation broth.

BACKGROUND

In the health care industry as well as in many other commercial and industrial applications, it is often necessary to monitor the effectiveness of processes used to sterilize equipment such as medical and non-medical devices, instruments and other articles and materials. A biological indicator including spores can be included in the batch of articles to be sterilized to assay the lethality of the sterilization process. Such a biological indicator can also be used to validate the effectiveness of sterilization equipment and sterilization cycles used in such equipment. Following the sterilization process, the spores of the biological indicator can be exposed to a growth media or other detection media for the purpose of determining the viability of the spores.

Spores are a highly resistant, dormant cells formed by some types of bacteria. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water, nor air for survival and is protected against a variety of trauma, including extremes of temperature, radiation, and chemical assault.

One type of method for producing spores used in connection with a biological indicator is a plate-based culture method in which bacterial cells are recovered from storage and cultured using a series of sets of Petri plates to produce spores that meet the desired product's acceptance criteria. The plate-based culture method is time consuming, labor intensive, and costly. It requires several rounds of culturing, which can take up to several months to complete, as well as several rounds of manual scraping of cells, collecting, centrifuging, decanting, washing, and re-plating. This iterative method also requires the use of many Petri plates and other equipment to effectuate the plating and incubation thereof.

For the spores to meet acceptance criteria, they must meet minimal resistance where they can survive a limited exposure to sterilization conditions, and must also fully expire prior to the completion of a cycle. However, the degree of resistance to sterilization can vary greatly between lots using the same plate-based culture method, and plate-based culture methods can also produce spores that fall throughout, and sometimes outside, the acceptance spectrum. It is a risk that a significant investment of resources including media, disposable Petri plates, personnel hours, incubator space, and months of punctuated incubation result in a lot outside of the control specifications, which must be discarded.

The yield of spores also may fluctuate greatly in a plate-based culture methods due to the complex nature of the media, exacerbated by the loss of culture homogeneity from the frozen stock during initial colony selection. Intra-culture dynamics during punctuated incubations on nutrient rich media may drive selection for a larger fraction of vegetative cells that fail to sporulate or fail to sporulate completely. If these events become dominant in a lot, they will drive the yield of spore per milliliter down. This can also result in a discarded lot.

SUMMARY OF THE INVENTION

The application relates to a liquid sporulation method and sporulation broth. The liquid sporulation method may provide for the reduction in lead time needed to produce a spore crop as compared with conventional plate-based methods, without compromising spore yield (cfu/mL) and performance of the spores. The method may also provide a significant reduction in associated costs needed to produce a spore suspension as compared with conventional plate methods, and may be scaled up with a minimal increase in required labor.

In accordance an aspect of the present disclosure, a liquid sporulation method includes: preparing a first liquid culture by adding bacterial cells to a sporulation broth, wherein an optical density ($OD_{600}$) of the first liquid culture as prepared is in a range of 0.001-0.01; incubating the first liquid culture such that an optical density ($OD_{600}$) of the first liquid culture is increased to be in a range of 0.2-2.0; preparing a second liquid culture by adding the incubated first liquid culture to a predetermined amount of additional sporulation broth, wherein an optical density ($OD_{600}$) of the second liquid culture as prepared is in the range of 0.001-0.1, and a ratio of a volume of the second liquid culture to a volume of the first liquid culture is in a range of 10:1-150:1; and incubating the second liquid culture such that an optical density ($OD_{600}$) of the second liquid culture is increased to be in a range of 1.0-4.0.

In some embodiments, the method further includes harvesting spores from the incubated second liquid culture. In some embodiments, the harvesting includes centrifuging the second liquid culture and separating the spores from resultant supernatant.

In some embodiments, the bacterial cells include *Geobacillus stearothermophilus*.

In some embodiments, the sporulation broth includes one or more types of metal ions, one or more types of mineral ions, one or more buffers, starch, trypticase peptone, and yeast extract dispersed in water.

In some embodiments, the one or more types of metal ions and the one or more types of mineral ions are from one or more dissociated inorganic salts provided in an amount falling in a range of 1 g/L to 20 g/L of the sporulation broth; the buffer is provided in an amount falling in a range of 1 g/L to 50 g/L of the sporulation broth; the starch is provided in an amount falling a range of 0.5 g/L to 20 g/L of the sporulation broth; and the trypticase peptone and the yeast extract are collectively provided in an amount falling in a range of 0.5 g/L to 30 g/L of the sporulation broth.

In some embodiments, the starch is provided in an amount falling a range of 2 g/L to 5 g/L of the sporulation broth.

In some embodiments, the sporulation broth of the first liquid culture and the additional sporulation broth of the second liquid culture have the same composition.

In some embodiments, a volume of the first liquid culture is in the range of 20 mL-75 mL.

In some embodiments, a volume of the second liquid culture is in the range of 700 mL-3000 mL.

In some embodiments, a volume of the second liquid culture is in the range of 700 mL-2400 mL.

In some embodiments, a volume of the second liquid culture is in the range of 700 mL-1600 mL.

In some embodiments, a volume of the second liquid culture is in the range of 750 mL-850 mL.

In some embodiments, a ratio of a volume of the second liquid culture to a volume of the first culture is in the range of 10:1-150:1.

In some embodiments, a ratio of the volume of a second liquid culture to the volume of a first culture is in the range of 10:1-80:1.

In some embodiments, a ratio of the volume of a second liquid culture to the volume of the first culture is in the range of 10:1-45:1.

In some embodiments, the incubation of the first liquid culture is conducted for a period of time falling in a range of 2 hours-8 hours.

In some embodiments, the incubation of the second liquid culture is conducted for a period of time falling in a range of 12 hours-48 hours.

In accordance with another aspect of the present disclosure, a sporulation broth includes: one or more types of metal ions, one or more types of mineral ions, one or more buffers, starch, trypticase peptone, and yeast extract dispersed in water, wherein: the one or more types of metal ions and the one or more types of mineral ions are from one or more dissociated inorganic salts provided in an amount falling in the range of 1 g/L to 20 g/L of the sporulation broth; the buffer is provided in an amount falling in a range of 1 g/L to 50 g/L of the sporulation broth; the starch is provided in an amount falling a range of 0.5 g/L to 20 g/L of the sporulation broth; and the trypticase peptone and the yeast extract are collectively provided in an amount falling in the range of 0.5 g/L to 30 g/L of the sporulation broth.

In some embodiments, the starch is provided in an amount falling the range of 2 g/L to 5 g/L of the sporulation broth.

In some embodiments, the one or more inorganic salts comprise one or more of ammonium sulfate ($NH_4SO_4$), magnesium sulfate ($MgSO_4$), manganese(II) sulfate ($Mn(II)SO_4$), iron(III) sulfate ($FeSO_4$), calcium sulfate ($CaSO_4$), potassium sulfate ($KSO_4$), and zinc sulfate ($ZnSO_4$).

In some embodiments, the one or more inorganic salts comprise one or more of potassium phosphate monobasic ($KH_2PO_4$), potassium phosphate dibasic ($K_2HPO_4$), iron phosphate ($Fe(III)PO_4$), calcium phosphate ($Ca(PO_4)_2$), tricalcium phosphate ($Ca_3(PO_4)_2$), magnesium ammonium phosphate ($MgNH_4PO_4$), sodium phosphate ($NaPO_4$), and zinc phosphate ($Zn(II)PO_4$).

In some embodiments, the one or more inorganic salts comprise one or more of calcium chloride ($CaCl_2$)), ammonium chloride ($NH_4Cl$), magnesium chloride ($MgCl_2$), sodium chloride ($NaCl_2$), iron chloride ($FeCl_3$), manganese chloride ($MnCl_2$), potassium chloride ($KCl$), and zinc chloride ($ZnCl_2$).

In some embodiments, the buffer comprises one or more of MOPS (3-(N-morpholino) propanesulfonic acid), citric acid ($C_6H_8O_7$), MES (2-(N-Morpholino)ethanesulfonic acid), BIS-TRIS ($C_8H_{19}NO_5$), PIPES (Piperazine-N,N'-bis(2-ethanesulfonic acid), MOPSO (3-morpholinopropane-sulfonic acid), BES (N,N-bis[2-hydroxyethyl]-2-aminoethanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid), and $KH_2PO_4$.

In some embodiments, the sporulation broth further includes one or more of casamino acid, proteose peptone, tryptose, casitone, beef extract, and phytone.

In some embodiments, a pH of the sporulation broth is in a range of 6.0-8.0.

The following description and the annexed drawing set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

DETAILED DESCRIPTION

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "biological indicator" refers to an article that can be used to determine the efficacy of a sterilization process. The biological indicator may include test microorganisms. The term "test microorganism" may refer to a microorganism that is more resistant to a sterilization process than the organisms intended for destruction during the sterilization process. In theory, if the test microorganisms were to die during the sterilization process, then all organisms intended for destruction during the sterilization process that were less resistant to the sterilization than the test microorganisms would also die. The test microorganisms may include a bacteria. The test microorganisms may include spores. The test microorganisms may include bacterial spores. The biological indicator may include the test microorganisms (e.g., bacteria, spores or bacterial spores) on a carrier. The biological indicator may include bacteria, the bacteria may be present within a defined space or deposited on a carrier. The biological indicator may include spores (e.g., bacterial spores), the spores may be present within a defined space or on a carrier. The biological indicator may include a spore strip.

The term "bacteria" refers to a domain of prokaryotic microorganisms.

The term "spore" refers to a non-reproductive dormant cell that may be adapted for dispersal and survival for extended periods of time under unfavorable conditions. Spores are highly resistant, dormant cell types. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault.

The term "bacterial spore" refers to a spore produced by bacteria.

The term "carrier" refers to a support onto which test microorganisms or spores are deposited to form a biological indicator.

The term "killing" test microorganisms or spores refers to rendering test microorganisms or spores incapable of reproduction, metabolism and/or growth. The term "dead" test microorganisms or spores refers to spores which have been rendered incapable of reproduction, metabolism and/or growth. The test microorganisms or spores used with the biological indicator are selected from those that would be more resistant to a sterilization process for which they are intended to monitor than the organisms to be killed by the sterilization process. The killing of the test microorganisms or spores on the biological indicator during the sterilization process is indicative of a successful sterilization process.

The term "sterilization" may be used to refer to a process wherein there is a total absence of living test microorganisms remaining after the sterilization process has been completed. However, processes that are less rigorous than sterilization processes including, for example, disinfection, sanitization, decontamination, cleaning processes, and the like, may be of value in that they significantly reduce the total number of viable organisms and are taken into account with the present disclosure. Unless otherwise indicated, the term "sterilization" is used herein to refer to sterilization processes as well as less rigorous processes such as disinfection, sanitation, decontamination, cleaning, and the like.

The term "sterilant" refers to any medium or energy that can be used to sterilize a substrate (e.g., a medical device, the interior of a room, etc.). The sterilant may include a liquid or a gas. The sterilant may include vaporous hydrogen peroxide, steam, ethylene oxide, peracetic acid, ozone, or a combination of two or more thereof. The sterilant may include ultraviolet light or radiation. The radiation may include x-ray radiation, gamma radiation, or electron beam radiation.

Figure 1:
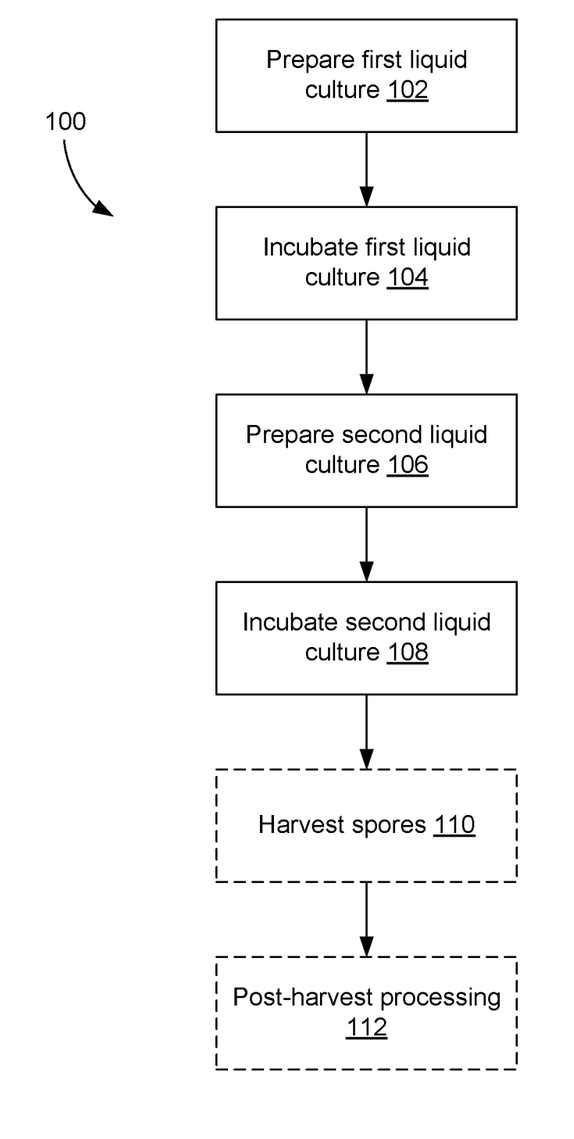
FIG. 1 is a flow chart showing an exemplary liquid sporulation method in connection with the present disclosure.

Turning now to FIG. 1, an exemplary liquid sporulation method is shown at 100. At step 102, a first liquid culture is prepared. The first liquid culture may be prepared by adding bacterial cells to a sporulation broth. This sporulation broth may also be referred to as a "liquid sporulation medium" or "aqueous dispersion". The sporulation broth may be formulated to support high cell density growth as well as sporulation of the bacterial cells.

The sporulation broth includes one or more components dispersed in water. In some embodiments, the water is deionized water or distilled water.

The sporulation broth may include one or more types of metal ions and/or one or more types of mineral ions. The metal ions and mineral ions may be provided by one or more types of inorganic salts (such as metal salts and/or other types of inorganic salts) that may dissociate in the sporulation broth. Examples include sulfates such as ammonium sulfate ($NH_4SO_4$), magnesium sulfate ($MgSO_4$), manganese (II) sulfate ($Mn(II)SO_4$), iron(III) sulfate ($FeSO_4$), calcium sulfate ($CaSO_4$), potassium sulfate ($KSO_4$), and zinc sulfate ($ZnSO_4$); phosphates such as potassium phosphate monobasic ($KH_2PO_4$), potassium phosphate dibasic ($K_2HPO_4$), iron phosphate ($Fe(III)PO_4$), calcium phosphate ($Ca(PO_4)_2$), tricalcium phosphate ($Ca_3(PO_4)_2$), magnesium ammonium phosphate ($MgNH_4PO_4$), sodium phosphate ($NaPO_4$), and zinc phosphate ($Zn(II)PO_4$); chlorides such as calcium chloride ($CaCl_2$)), ammonium chloride ($NH_4Cl$), magnesium chloride ($MgCl_2$), sodium chloride ($NaCl_2$), iron chloride ($FeCl_3$), manganese chloride ($MnCl_2$), potassium chloride ($KCl$), and zinc chloride ($ZnCl_2$); and combinations thereof.

In some embodiments, the total amount of inorganic salts added to the sporulation broth may fall in the range of 1 g/L to 20 g/L of the sporulation broth. In other embodiments, the total amount of inorganic salts added to the sporulation broth may fall in the range of 2.5 g/L to 15 g/L of the sporulation broth. In other embodiments, the total amount of inorganic salts added to the sporulation broth may fall in the range of 5 g/L to 10 g/L of the sporulation broth.

The sporulation broth may include one or more types of buffers. Exemplary buffers include MOPS (3-(N-morpholino) propanesulfonic acid), citric acid ($C_6H_8O_7$), MES (2-(N-Morpholino)ethanesulfonic acid), BIS-TRIS ($C_8H_{19}NO_5$), PIPES (Piperazine-N,N'-bis(2-ethanesulfonic acid), MOPSO (3-morpholinopropanesulfonic acid), BES (N,N-bis[2-hydroxyethyl]-2-aminoethanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid), $KH_2PO_4$, and combinations thereof.

In some embodiments, the total amount of buffer in the sporulation broth may fall in the range of 1 g/L to 50 g/L of the sporulation broth. In other embodiments, the total amount of buffer in the sporulation broth may fall in the range of 10 g/L to 30 g/L of the sporulation broth. In other embodiments, the total amount of buffer in the sporulation broth may fall in the range of 15 g/L to 25 g/L of the sporulation broth.

The sporulation broth may include starch. Starch is a carbon source that may support high levels of sporulation in the culturing of the bacterial cells. In some embodiments, the sporulation broth may include one or more additional types of carbon sources. Exemplary additional carbon sources include saccharides such as glucose, sucrose, lactose, galactose, and maltose. In other embodiments, such additional carbon sources are not included in the sporulation broth.

In some embodiments, the total amount of carbon source (e.g., the starch and/or the additional carbon source(s)) in the sporulation broth may fall in the range of 0.5 g/L to 20 g/L of the sporulation culture. In other embodiments, the total amount of carbon source in the sporulation broth may fall in the range of 1 g/L to 10 g/L of the sporulation broth. In other embodiments, the total amount of carbon source in the sporulation broth may fall in the range of 2 g/L to 5 g/L of the sporulation broth.

The sporulation broth may include one or more complex components. Exemplary complex components include trypticase peptone and yeast extract, which are components that have less defined characteristics. Trypticase peptone is the pancreatic digest of casein and may serve as a nitrogen source (peptones) for the cells, among other nutrients. Yeast extracts are concentrates from the water-soluble portion of autolyzed yeast cells and may provide vitamins, amino acids, and peptides, along with other nutrients, to the media formulation. Other exemplary complex components include components that provide peptones, amino acids, and/or peptides, such as casamino acids, proteose peptone, tryptose, casitone, beef extract, phytones, and combinations thereof.

In some embodiments, the total amount of complex components (e.g., the trypticase peptone, yeast extract, and/or other complex components) in the sporulation broth may fall in the range of 0.5 g/L to 40 g/L of the sporulation broth. In other embodiments, the total amount of complex components in the sporulation broth may fall in the range of 5 g/L to 30 g/L of the sporulation broth. In other embodiments, the total amount of complex components in the sporulation broth may fall in the range of 15 g/L to 25 g/L of the sporulation broth.

Upon addition of the components to the water, the pH of the sporulation broth may be adjusted. In some embodiments, the pH of the sporulation broth may be adjusted using a pH adjusting compound such as potassium hydroxide (KOH), calcium hydroxide ($Ca(OH)_2$), and/or sodium hydroxide (NaOH). As an example, the pH of the sporulation broth may be (or may be adjusted to be) in a range of 6.0-8.0. In other embodiments, the pH of the sporulation broth may be (or may be adjusted to be) in a range of 6.5-7.5. In other embodiments, the pH of the sporulation broth may be (or may be adjusted to be) about 7.0.

Table 1 provides an exemplary sporulation broth formulation that includes the identified components dispersed in water.

TABLE 1

Exemplary sporulation broth formulation

| Component | Concentration (g/L) |
|---|---|
| MOPS (3-(N-morpholino) propanesulfonic acid) | 1.0-30.0 |
| Potassium Phosphate Monobasic ($KH_2PO_4$) | 0.1-1.5 |
| Potassium Phosphate Dibasic ($K_2HPO_4$) | 0.25-2 |
| Ammonium Sulfate ($NH_4SO_4$) | 0.5-3 |
| Magnesium Sulfate ($MgSO_4$) | 0.5-3 |
| Calcium Chloride ($CaCl_2$) | 0.01-0.15 |
| Manganese Chloride ($MnCl_2$) | 0.001-0.5 |
| Iron Chloride ($FeCl_2$) | 0.0001-0.005 |
| Zinc Sulfate ($ZnSO_4$) | 0.00001-0.0005 |
| Yeast Extract | 0.1-15 |
| Trypticase Peptone | 5.0-25.0 |
| Starch | 1.0-6.0 |

**pH adjusted to within the range of 6.0-8.0 with KOH

The bacterial cells may be vegetative cells selected from the genus *Geobacillus, Bacillus*, and *Clostridium*. In some embodiments, the bacterial cells are of a single species of bacteria. In other embodiments, the bacterial cells are a combination of two or more species and/or strains of bacteria. In some embodiments, the bacterial cells may be genetically modified bacterial cells. Exemplary genetically modified bacterial cells (and spores formed therefrom) are disclosed in U.S. Pat. Nos. 8,372,624 and 9,416,393, the disclosure of which are hereby incorporated by reference in their entireties.

Examples of bacteria belonging to the genus *Bacillus* include, but are not limited to, *Bacillus subtilis, Bacillus amyloliquefaciens, Bacillus pumilus, Bacillus lentus, Bacillus laterosporus, Bacillus alvei, Bacillus anthracis, Bacillus popilliae, Bacillus licheniformis, Bacillus coagulans, Bacillus subtilis globigii, Bacillus cereus, Bacillus circulans, Bacillus halodurans, Bacillus subtilis natto, Bacillus acidicola, Bacillus acidopullulyticus, Bacillus acidovorans, Bacillus aeolius, Bacillus aestuarii, Bacillus agaradhaerens, Bacillus akibai, Bacillus alcaliinulinus, Bacillus alcalophilus, Bacillus algicola, Bacillus alkalitolerans, Bacillus alkalogaya, Bacillus alveayuensis, Bacillus amiliensis, Bacillus aminovorans, Bacillus aquimais, Bacillus arbutinivorans, Bacillus arenosi, Bacillus arseniciselenatis, Bacillus arsenicus, Bacillus arvi, Bacillus asahii, Bacillus atrophaeus, Bacillus axarquiensis, Bacillus azotoformans, Bacillus badius, Bacillus baekryungensis, Bacillus barbaricus, Bacillus bataviensis, Bacillus benzoevorans, Bacillus bogoriensis, Bacillus borophilicus, Bacillus borotolerans, Bacillus caldolyticus, Bacillus caldotenax, Bacillus caldovelox, Bacillus carboniphilus, Bacillus casamancensis, Bacillus catenulatus, Bacillus cellulosilyticus, Bacillus sphaeicus, Bacillus thuringiensis*, and *Bacillus clausii*.

Examples of bacteria belonging to the genus *Clostridium* include, but are not limited to, *Clostridium sporogenes, Clostridium difficile*, and *Clostridium botulinum*, or a combination of two or more thereof.

Examples of bacteria belonging to the genus *Geobacillus* include, but are not limited to, *Geobacillus anatolicus, Geobacillus kaue, Geobacillus caldoproteolyticus, Geobacillus caldoxylosilyticus, Geobacillus debilis, Geobacillus gargensis, Geobacillus kaustophilus, Geobacillus stearothermophilus, Geobacillus thermocatenulatus, Geobacillus*

*thermodenitrificans, Geobacillus thermoglucosidasius, Geobacillus thermoleovorans, Geobacillus uralicus, Geobacillus uzenensis,* and *Geobacillus vulcani.*

In some embodiments, *Geobacillus stearothermophilus* is the bacteria strain combined with the sporulation culture to form the first liquid culture. The *Geobacillus stearothermophilus* used may be equivalent to *Geobacillus stearothermophilus* NRRL Culture Collection strain B-1172. The vegetative form of *Geobacillus stearothermophilus* is rod-shaped cells that produce one endospore per cell. The cell length ranges from 2.0-3.5 micrometers with a cell width ranging from 0.6-1.0 micrometers.

The bacterial cells may be provided from any suitable source, such as an existing stock of bacteria. The bacterial cells may be provided in a solution/suspension, or a lyophilized pellet, which may serve as an inoculum source that is added to the sporulation broth.

In some embodiments, cryogenically frozen cells may be thawed and prepared for addition to the aqueous dispersion. For example, one or more vials of the cryogenically frozen cells may be removed from cryostorage, warmed to room temperature (e.g., 21° C.), and then mixed on a vortex mixer. A vial may have, for example, $1.0 \times 10^7$-$1.0 \times 10^8$ cfu/mL bacterial cells. In some embodiments, at least 70% of the bacterial cells from the vial are vegetative cells. The bacterial cells may be dispersed in a solution such as glycerol. The contents of the one or more cryovials may then be centrifuged, and the bacteria may be separated from the resultant supernatant (e.g., by decanting) and resuspended in a medium such as water for injection (WFI) or an aliquot of the aqueous dispersion. The prepared bacterial cells may serve as an inoculum source.

In other embodiments, cryogenically frozen bacterial cells may be thawed and directly added to the aqueous dispersion. For example, one or more vials of the cryogenically frozen bacterial cells may be removed from cryostorage, warmed to room temperature (e.g., 21° C.), and the contents of the vial may be directly added to the broth. A vial may have, for example, $1.0 \times 10^7$-$1.0 \times 10^8$ cfu/mL bacterial cells dispersed in a solution such as glycerol. In some embodiments, at least 70% of the bacterial cells from the vial are vegetative cells.

The first liquid culture may have an optical density ($OD_{600}$) falling in the range of 0.001-0.1 In other embodiments, the first liquid culture may have an optical density ($OD_{600}$) falling in the range of 0.005-0.015. In other embodiments, the first liquid culture may have an optical density ($OD_{600}$) falling in the range of 0.008-0.013.

The OD of the first liquid culture is a function of the cell density of the bacteria present in the culture. Accordingly, the respective volumes of the sporulation broth and bacteria may be selected to yield an initial OD falling within the range. In some embodiments, the first culture is formed of a volume of liquid dispersion in a range of 20 mL-75 mL and a volume of the inoculum source in a range of 0.1 mL-2.5 mL. The culture may be an aliquot from a larger mixture having a ratio of liquid dispersion to inoculum such that the above ranges are satisfied.

At step 104, the first liquid culture is incubated. During the incubation period, the bacterial cells of the liquid culture may grow and sporulate in the broth.

The first liquid culture may be incubated in conditions to effect growth and sporulation of the bacteria. In some embodiments, the incubation temperature may be in the range of 35° C.-70° C. In other embodiment, the incubation temperature may be in the range of 40° C.-65° C. In other embodiment, the incubation temperature may be in the range of 55° C.-65° C.

The first liquid culture may be shaken during incubation. In some embodiments, the rate of shaking may fall in the range of 50 rpm-400 rpm. In other embodiments, the rate of shaking may fall in the range of 100 rpm-300 rpm. In other embodiments, the rate of shaking may fall in the range of 150 rpm-250 rpm.

The vessel in which the first liquid culture is incubated may also assist in stirring/agitation of the culture. For example, in some embodiments, the vessel in which the first liquid culture is incubated may be a baffled Erlenmeyer flask. In other embodiments, the vessel in which the first liquid culture is incubated may be an unbaffled Erlenmeyer flask.

During incubation, one or more properties of the first liquid culture may be periodically measured. Such properties include OD, pH, and/or observation under the microscope of the percentage of the culture that has sporulated.

In some embodiments, the culture may be incubated for a predetermined period of time. As an example, the incubation period may be for a period of time falling in the range of 2 hours-8 hours. In another example, the incubation period may be for a period of time falling in the range of 3 hours-5 hours. As another example, the incubation period may be for 4 hours.

In some embodiments, the duration of the incubation period may be at least in part dependent on the OD of the culture. Once a predetermined OD is reached, the incubation period may be ended. As an example, the predetermined OD ($OD_{600}$) may fall in the range of 0.2-2.0. As another example, the predetermined OD ($OD_{600}$) may fall in the range of 0.5-1.5. As another example, the predetermined OD ($OD_{600}$) may fall in the range of 0.75-1.0.

At step 106, a second liquid culture is produced. The second liquid culture may be produced by adding the incubated first culture to a predetermined amount of additional sporulation broth. The additional sporulation broth may be the same medium used in step 102. In some embodiments, the additional sporulation broth may differ in one or more of the ingredients and/or amounts as compared with the medium used in step 102.

The amount of additional sporulation broth added may be calculated such that the second culture has a predetermined OD. In some embodiments, the second liquid culture may have an optical density ($OD_{600}$) falling in the range of 0.001-0.1. In other embodiments, the second liquid culture may have an optical density ($OD_{600}$) falling in the range of 0.005-0.015. In other embodiments, the second liquid culture may have an optical density ($OD_{600}$) falling in the range of 0.008-0.013.

The OD of the second liquid culture is a function of the cell density of the bacteria present in the culture. Accordingly, the volumes of the additional sporulation broth added to the first culture may be selected to yield an initial OD falling within the desired range. In some embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is in the range of 700 mL-3000 mL. In other embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is in the range of 700 mL-2400 mL. In other embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is in the range of 700 mL-1600 mL. In other embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is in the range of 700 mL-1000 mL. In other embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is in the range of 750 mL-850 mL. In other embodiments where the first culture is formed of a volume of sporulation broth in a range of 20 mL-75 mL and a volume of the inoculum source in a range of 0.1 mL-2.5 mL, the additional sporulation broth may be added in an amount such that the volume of the second culture is 800 mL. The second culture may be provided in a single vessel, or may be divided up into two or more aliquots. The aliquots may be divided up into two or more vessels (e.g., flasks) for subsequent incubation.

In some embodiments, the ratio of the volume of the second culture to the volume of the first culture is in the range of 10:1-150:1. In other embodiments, the ratio of the volume of the second culture to the volume of the first culture is in the range of 10:1-120:1. In other embodiments, the ratio of the volume of the second culture to the volume of the first culture is in the range of 10:1-80:1. In other embodiments, the ratio of the volume of the second culture to the volume of the first culture is in the range of 10:1-50:1. In other embodiments, the ratio of the volume of the second culture to the volume of the first culture is in the range of 10:1-45:1. In other embodiments, the ratio of the volume of the second culture to the volume of the first culture is in the range of 10:1-40:1.

At step 108, the second liquid culture is incubated for a predetermined period of time. During the incubation period, the bacterial cells of the liquid culture may grow and sporulate in the broth.

The second liquid culture may be incubated in conditions to effect growth and sporulation of the bacteria. In some embodiments, the incubation temperature may be in the range of 35° C.-70° C. In other embodiment, the incubation temperature may be in the range of 40° C.-65° C. In other embodiment, the incubation temperature may be in the range of 55° C.-65° C.

The second liquid culture may be shaken during incubation. In some embodiments, the rate of shaking may fall in the range of 50 rpm-400 rpm. In other embodiments, the rate of shaking may fall in the range of 100 rpm-300 rpm. In other embodiments, the rate of shaking may fall in the range of 150 rpm-250 rpm.

The vessel in which the second liquid culture is incubated may also assist in stirring/agitation of the culture. For example, in some embodiments, the vessel in which the first liquid culture is incubated may be a baffled Erlenmeyer flask. In other embodiments, the vessel in which the first liquid culture is incubated may be an unbaffled Erlenmeyer flask.

During incubation, one or more properties of the second liquid culture may be periodically measured. Such properties include OD, pH, and/or observation under the microscope of the percentage of the culture that has sporulated.

In some embodiments, the culture may be incubated for a predetermined period of time. As an example, the incubation period may be for a period of time falling in the range of 12 hours-48 hours. In another example, the incubation period may be for a period of time falling in the range of 20 hours-28 hours. As another example, the incubation period may be for 24 hours.

In some embodiments, the duration of the incubation period may be at least in part dependent on the OD of the culture. Once a predetermined OD is reached, the incubation period may be ended. As an example, the predetermined OD ($OD_{600}$) may fall in the range of 1.0-4.0. As another example, the predetermined OD ($OD_{600}$) may fall in the range of 1.5-3.5. As another example, the predetermined OD ($OD_{600}$) may fall in the range of 1.5-3.

Optionally, at step 110, the spores are harvested. The second culture may be centrifuged, and the spores may be separated from the resultant supernatant (e.g., by decanting). In some embodiments, the spores may be resuspended in a medium such as WFI, water for irrigation, deionized water, and/or tap water.

In other embodiments, step 110 is omitted. In such embodiments, the incubated culture can be directly subjected to one or more post-sporulation steps (e.g., heat shock) if included as part of the process.

Optionally, at step 112, the spore suspension may be subjected to one or more post-sporulation steps. In some embodiments, the spore suspension may be washed one or more times. Washing may be conducted using WFI, water for irrigation, deionized water, and/or tap water. In other embodiments, the spores may be subjected to one or more heat shock procedures. In an exemplary heat shock process, a water bath may be provided at a predetermined elevated temperature (e.g., 80° C., 100° C., etc.) and the vessel containing the spore suspension may be immersed in the water bath for a predetermined amount of time, or for a given amount of time for the spore suspension to reach a predetermined temperature. In some embodiments, the vessel containing the spore suspension may be immersed in the water bath for a time in the range of 5 minutes-60 minutes. In other embodiments, the vessel containing the spore suspension may be immersed in the water bath for a time in the range of 10 minutes-30 minutes. In other embodiments, the vessel containing the spore suspension may be immersed in the water bath for a time in the range of 10 minutes-20 minutes.

The process for producing a bacterial spore suspension in accordance with the present disclosure may provide one or more advantages. For example, the process may allow for the reduction in lead time needed to produce a spore crop as compared with conventional plate processes. The agar plate process requires about 40 days to achieve the same output the liquid system may achieve in, for example, 1 to 2 days. The shortened timeframe of the process may also be accomplished without compromising spore yield (cfu/mL) and performance of the spores to steam sterilization, as measured by D value (decimal reduction time needed to kill 1 log of exposed organism).

The process for producing a bacterial spore suspension in accordance with the present disclosure may also provide a significant reduction in associated costs needed to produce a spore suspension as compared with conventional plate processes. The process may provide an estimated 90% decrease in lead time, which equates to less personnel hours needed as well as less consumable supplies. The process may obviate the need hundreds of petri dishes, liters of different media types, as well as labor intensive harvesting and processing steps.

The process for producing a bacterial spore suspension in accordance with the present disclosure may also be scaled up with a minimal increase in required labor. For example, production of the second culture may have the flexibility to double or triple its volume simply by incubating the first culture for a time period such that the final OD of the first culture allows for dilution of the first culture in the sporulation broth to a larger volume while hitting the same desired initial OD for the second culture.

The bacterial spore suspension may be used in the manufacture of a biological indicator. The biological indicator may comprise test microorganisms (e.g., spores) deposited on a carrier. The spore population for the biological indicator may be in the range from about 500,000 to about 4,000,000 spores, or from about 500,000 to about 2,500,000 spores, or from about 500,000 to about 1,500,000 spores, or from about 750,000 to about 1,200,000 spores or about $10^6$ cfu. The carrier may comprise a vial, strip, sheet or film of any material that does not dissolve or deteriorate during the sterilization processes. The carrier may comprise paper, e.g., cellulose, plastic, glass, ceramic, metal, or a combination of two or more thereof. The plastic may comprise a polyolefin, polypropylene, polystyrene, polycarbonate, polymethacrylate, polyacrylamide, polyimide, polyester, or a combination of two or more thereof.

In some embodiments, the carrier on which the test microorganisms (e.g., spores) are deposited may be a plastic or glass vial as in a self-contained biological indicator (SCBI). For example, the vial may be made of polypropylene. One example of a SCBI is the Celerity™ 20 STEAM SCBI supplied by STERIS Corporation. These SCBI's are characterized by spore populations of at least about $10^6$ Geobacillus stearothermophilus spores per test strip.

In other embodiments, the carrier on which the test microorganisms (e.g., spores) are deposited may be a spore test strip. One example of a spore test strip is the VERIFY® Spore Test Strip for S40® Sterilant Concentrate supplied by STERIS Corporation. These test strips are cellulose strips that are 0.6 cm wide, 3.8 cm long, and less than 0.1 cm thick. These test strips are characterized by spore populations of at least about $10^5$ Geobacillus stearothermophilus spores per test strip.

The biological indicator may be used to determine the effectiveness of a sterilization process. The sterilization process may involve exposing an article to be sterilized as well as the above-indicated biological indicator to a sterilization medium, and subsequently exposing the spores to a growth medium or other suitable detection medium and monitoring for the detection (or absence thereof) of outgrowth of the spores (or the presence of an indicator such as an enzyme from viable spores cleaving a fluorogenic substrate). The sterilization process may be conducted for an effective period of time to achieve at least a 4 log reduction, or at least a 5 log reduction, or at least a 6 log reduction in the number of test microorganisms capable of reproduction, metabolism and/or growth. When at least a 6 log reduction is achieved, the process may be referred to as a sterilization process.

The biological indicator of the present invention may be used to examine the lethality of one or more sterilants against any microorganism with less resistance to the sterilization process than the host organism. These microorganisms may include bacteria such as Escherichia coli, Legionella sp., Campylobacter sp., and other enteric bacteria, as well as Staphylococcus and Streptococcus species and other human pathogenic microorganisms such as Cryptosporidium.

Example 1—Preparation and Testing of Seed Cultures

Three cryovials, each containing a 1 mL of Geobacillus stearothermophilus in glycerol, are removed from cryostorage, allowed to warm to room temperature (21° C.), and then mixed on a vortex mixer. The contents of the three cryovials are then transferred to a single 15 mL falcon tube and centrifuged at 4500 rpm for 10 minutes. The glycerol supernatant is decanted and the Geobacillus stearothermophilus is resuspended in water for injection (WFI) and mixed on a vortex mixer to create a inoculum source.

Sporulation broth is prepared that includes the formulation set forth in Table 2. The identified components are added to deionized water and then the volume is increased to 100 mL such that the components are provided at the listed concentrations.

TABLE 2

Sporulation broth formulation

| Component | Concentration (g/L) |
|---|---|
| MOPS (3-(N-morpholino) propanesulfonic acid) | 21.0 |
| Potassium Phosphate Monobasic ($KH_2PO_4$) | 0.29 |
| Potassium Phosphate Dibasic ($K_2HPO_4$) | 0.77 |
| Ammonium Sulfate ($NH_4SO_4$) | 1.32 |
| Magnesium Sulfate ($MgSO_4$) | 1.20 |
| Calcium Chloride ($CaCl_2$) | 0.08 |
| Manganese Chloride ($MnCl_2$) | 0.01 |
| Iron Chloride ($FeCl_3$) | 0.001 |
| Zinc Sulfate ($ZnSO_4$) | 0.0001 |
| Yeast Extract | 1.0 |
| Trypticase Peptone | 20.0 |
| Starch | 4.0 |

**pH adjusted to 7.0 with 2M KOH solution 98 mL of the sporulation broth is transferred to an Erlenmeyer flask and 2 mL of the inoculum source is added to create a liquid culture. The liquid culture is mixed and then transferred to two 250 mL baffled Erlenmeyer flasks such that each flask includes a 50 mL aliquot (cultures A and B).

A control culture is prepared in a 250 mL baffled Erlenmeyer flask by adding 49 mL tryptic soy broth (TSB) and 1 mL of the inoculum source to the flask. The control culture is mixed.

The three flasks are incubated at 57° C. while being shaken at 200 rpm. Measurements of the optical density ($OD_{600}$) and pH are periodically taken, which are shown in Table 3.

TABLE 3

Measurements

| Elapsed Time | Measurement | A Culture | B Culture | Control Culture |
|---|---|---|---|---|
| Initial | OD | 0.011 | 0.011 | 0.011 |
| (0 hours) | pH | 6.8 | 6.8 | 6.9 |
| 1.5 hours | OD | 0.033 | 0.031 | 0.009 |
|  | pH | 6.7 |  |  |
| 2.5 hours | OD | 0.151 | 0.137 | 0.074 |
|  | pH |  |  |  |
| 4 hours | OD | 0.804 | 0.804 | 0.789 |
|  | pH | 6.4 | 6.4 | 6.0 |
| 5 hours | OD | 1.17 | 1.19 | 1.16 |
|  | pH | 6.4 | 6.4 | 6.0 |
| 6 hours | OD | 1.50 | 1.54 | 1.24 |
|  | pH |  |  |  |
| 7 hours | OD | 1.72 | 1.76 | 1.40 |
|  | pH | 6.2 | 6.0 | 5.9 |

Example 2—Preparation and Testing of Seed Cultures

Sporulation broth is prepared that includes the formulation set forth in Table 5. The identified components are added to 80 mL deionized water and then the volume is increased to 100 mL such that the components are provided at the listed concentrations.

TABLE 5

Sporulation broth formulation

| Component | Concentration (g/L) |
| --- | --- |
| MOPS (3-(N-morpholino) propanesulfonic acid) | 21.0 |
| Potassium Phosphate Monobasic ($KH_2PO_4$) | 0.29 |
| Potassium Phosphate Dibasic ($K_2HPO_4$) | 0.77 |
| Ammonium Sulfate ($NH_4SO_4$) | 1.32 |
| Magnesium Sulfate ($MgSO_4$) | 1.20 |
| Calcium Chloride ($CaCl_2$) | 0.08 |
| Manganese Chloride ($MnCl_2$) | 0.01 |
| Iron Chloride ($FeCl_3$) | 0.001 |
| Zinc Sulfate ($ZnSO_4$) | 0.0001 |
| Yeast Extract | 1.0 |
| Trypticase Peptone | 10.0 |
| Starch | 2.0 |

**pH adjusted to 7.0 with 2M KOH solution

Two cryovials, each containing a 1 mL of *Geobacillus stearothermophilus* in glycerol, are removed from cryostorage, allowed to warm to room temperature (21° C.), and then mixed on a vortex mixer. The contents of the two cryovials are then transferred to a single 15 mL falcon tube and centrifuged at 5000 rpm for 3 minutes. The glycerol supernatant is decanted and the *Geobacillus stearothermophilus* is resuspended in 1 mL of the sporulation broth and mixed on a vortex mixer to create a inoculum source.

The sporulation broth is transferred to an Erlenmeyer flask and the inoculum source is added to create a liquid culture. The liquid culture is mixed and then transferred to two 250 mL baffled Erlenmeyer flasks such that each flask includes a 50 mL aliquot (cultures A and B).

The two flasks are incubated at 57° C. while being shaken at 200 rpm. The initial optical density ($OD_{600}$) is 0.012. After 7 hours of incubation, wet mount slides were prepared from a sample taken from each of cultures A and B and observed under the microscope. The 7 hour samples from both of cultures A and B are both observed as having a good number of sporangia, about 25%-50% of the population. The cultures look healthy.

After 23 hours of incubation, wet mount slides were prepared from a sample taken from each of cultures A and B and observed under the microscope. The 23 hour sample from culture A is observed as having very good sporulation, not many vegetative bacteria, and the vegetative bacteria look very faint and granulated. The 23 hour sample from culture B is observed as having very good sporulation, spores having a faint tail, with slightly more vegetative bacteria than culture B.

After the 23 hour measurement, the spores in cultures A and B are harvested. Each flask is centrifuged for 10 minutes at 4700 rpm, resuspended in equal volume WFI, and heat shocked for 15 minutes at 100° C. The harvest volume for culture A is 36 mL and the pH of the harvested culture A is 7.0. The harvest volume for culture B is 36 mL and the pH of the harvested culture B is 7.0.

The harvested culture A and the harvested culture B are both subjected to spore titer testing. Culture A and culture B are serial diluted in WFI down to −6 dilution. Three plates are prepared of 1 mL −6 diluted culture A on TSA, and three plates are prepared of 1 mL −6 diluted culture B on TSA. Population results of the spore titer testing after two days are shown in Table 6.

TABLE 6

Measurement at 24 hours

| Culture | Dilution | Volume | Individual Result (cfu/mL) | Average (cfu/mL) |
| --- | --- | --- | --- | --- |
| A | −6 | 1 mL | 1.53E8 | 1.57E8 |
|   |   |   | 1.70E8 |   |
|   |   |   | 1.47E8 |   |
| B | −6 | 1 mL | 1.53E8 | 1.38E8 |
|   |   |   | 1.24E8 |   |
|   |   |   | 1.36E8 |   |

Example 3—Testing of Carbon Sources

Sporulation broth is prepared that includes the formulation set forth in Table 7. The identified components are added to 800 mL deionized water and then the volume is increased to 1000 mL such that the components are provided at the listed concentrations.

TABLE 7

Sporulation broth formulation

| Component | Concentration (g/L) |
| --- | --- |
| MOPS (3-(N-morpholino) propanesulfonic acid) | 21.0 |
| Potassium Phosphate Monobasic ($KH_2PO_4$) | 0.29 |
| Potassium Phosphate Dibasic ($K_2HPO_4$) | 0.77 |
| Ammonium Sulfate ($NH_4SO_4$) | 1.32 |
| Magnesium Sulfate ($MgSO_4$) | 1.20 |
| Calcium Chloride ($CaCl_2$) | 0.08 |
| Manganese Chloride ($MnCl_2$) | 0.01 |
| Iron Chloride ($FeCl_3$) | 0.001 |
| Zinc Sulfate ($ZnSO_4$) | 0.0001 |
| Yeast Extract | 1.0 |
| Trypticase Peptone | 10.0 |

**pH adjusted to 7.0 with 2M KOH solution

A cryovial containing a 1 mL of *Geobacillus stearothermophilus* in glycerol is removed from cryostorage, allowed to warm to room temperature (21° C.), and then mixed on a vortex mixer. The contents of the cryovial are then transferred to a single 15 mL falcon tube and centrifuged at 5000 rpm for 2 minutes. The glycerol supernatant is decanted and the *Geobacillus stearothermophilus* is resuspended in sporulation broth and mixed on a vortex mixer to create a inoculum source.

Cultures are prepared in baffled Erlenmeyer flasks in accordance with Table 8 and inoculated using the inoculum source.

TABLE 8

Culture preparations

| Culture | Sporulation Broth | Maltose Stock | Starch Stock |
| --- | --- | --- | --- |
| A | 51 mL | 0.1 mL |   |
| B | 51 mL | 1 mL |   |
| C | 51 mL |   | 0.5 mL |
| D | 51 mL |   | 5 mL |

The three flasks are incubated at 57° C. while being shaken at 200 rpm. Measurements of the optical density ($OD_{600}$) and pH are periodically taken, which are shown in Table 2. When measuring at the 6 hour and 23 hour marks, wet mount slides were prepared from a sample taken from each of cultures A-D and observed under the microscope. The 6 hour sample from each of cultures A-D are observed as having mostly vegetative bacteria, but a good number of sporangia. The 23 hour sample for culture A is observed as having very little vegetative bacteria, with a moderate number of almost free spores. The 23 hour sample for culture B is observed as having lots of unhealthy intact, flocculated vegetative bacteria, and the spores have more intact sporangia. The 23 hour sample of cultures C and D are observed as having a good amount of almost free spores, and a low amount of intact vegetative bacteria.

TABLE 9

Measurements

| Elapsed Time | Measurement | A Culture | B Culture | C Culture | D Culture |
|---|---|---|---|---|---|
| Initial (0 hours) | OD | 0.01 | 0.01 | 0.01 | 0.01 |
| | pH | | | | |
| 6 hours | OD | 1.3 | 3.11 | 1.46 | 0.338 |
| | pH | 6.8 | 6.4 | 6.8 | 6.3 |
| 23 hours | OD | 0.99 | 2.35 | 1.61 | 2.088 |
| | pH | 6.5 | 5.0 | 6.5 | |

After the 23 hour measurement, the spores in cultures A and B are harvested. Cultures A-D are transferred to respective Falcon tubes and centrifuged for 10 minutes at 4500 rpm, resuspended in equal volume WFI, vortex mixed, and heat shocked for 15 minutes at 100° C. The harvest volume for culture A is 43 mL, the harvest volume for culture B is 43 mL, the harvest volume for culture C is 43 mL, and the harvest volume for culture D is 47 mL.

For each harvested culture A-D, a respective 10 mL aliquot is heat shocked for 15 minutes at 100° C. After the heat shock, the 10 mL aliquots are subjected to spore titer testing. Each of the 10 mL aliquots are serial diluted in WFI down to −5 dilution. Three plates are prepared of 1 mL −5 diluted culture A on TSA, three plates are prepared of 1 mL −5 diluted culture B on TSA, three plates are prepared of 1 mL −5 diluted culture C on TSA, and three plates are prepared of 1 mL −5 diluted culture D on TSA. Population results of the spore titer testing after two days are shown in Table 10.

TABLE 10

Measurement at 24 hours

| Culture | Dilution | Volume | Individual Result (cfu/mL) | Average (cfu/mL) |
|---|---|---|---|---|
| A | −5 | 1 mL | 5.4E6 | 5.87E6 |
| | | | 6.4E6 | |
| | | | 5.8E6 | |
| B | −5 | 1 mL | 1.15E7 | 1.19E7 |
| | | | 1.31E7 | |
| | | | 1.10E7 | |
| C | −5 | 1 mL | 1.28E7 | 1.26E7 |
| | | | 1.27E7 | |
| | | | 1.23E7 | |
| D | −5 | 1 mL | 1.33E7 | 1.27E7 |
| | | | 1.38E7 | |
| | | | 1.10E7 | |

As shown, the cultures including starch as part of the broth formulation provides a higher yield of spores as compared with the cultures including maltose as part of the broth formulation.

While the present disclosure has been explained in relation to various embodiments, it is to be understood that various modifications thereof will become apparent to those skilled in the art upon reading the specification. Therefore, it is to be understood that the disclosure described herein includes any such modifications that may fall within the scope of the appended claims.

The invention claimed is:

1. A liquid sporulation method, comprising:
    preparing a first liquid culture by adding bacterial cells to a sporulation broth, wherein an optical density ($OD_{600}$) of the first liquid culture as prepared is in a range of 0.001-0.015;
    incubating the first liquid culture such that an optical density ($OD_{600}$) of the first liquid culture is increased to be in a range of 0.2-2.0, wherein the bacterial cells in the first liquid culture grow and sporulate during the incubation of the first liquid culture;
    preparing a second liquid culture by adding the incubated first liquid culture to additional sporulation broth, wherein an optical density ($OD_{600}$) of the second liquid culture as prepared is in the range of 0.001-0.1, and a ratio of a volume of the second liquid culture to a volume of the first liquid culture is in a range of 10:1-150:1;
    incubating the second liquid culture such that an optical density ($OD_{600}$) of the second liquid culture is increased to be in a range of 1.0-4.0, wherein the bacterial cells in the second liquid culture grow and sporulate during the incubation of the second liquid culture; and
    harvesting spores from the incubated second liquid culture, wherein the harvesting comprises centrifuging the second liquid culture to form a supernatant and separating the spores from the supernatant.

2. The method of claim 1, wherein the bacterial cells comprise *Geobacillus stearothermophilus*.

3. The method of claim 1, wherein the sporulation broth comprises one or more types of metal ions, one or more types of mineral ions, one or more buffers, starch, trypticase peptone, and yeast extract dispersed in water.

4. The method of claim 3, wherein:
    the one or more types of metal ions and the one or more types of mineral ions are from one or more dissociated inorganic salts provided in an amount falling in a range of 1 g/L to 20 g/L of the sporulation broth;
    the buffer is provided in an amount falling in a range of 1 g/L to 50 g/L of the sporulation broth;
    the starch is provided in an amount falling a range of 0.5 g/L to 20 g/L of the sporulation broth; and
    the trypticase peptone and the yeast extract are collectively provided in an amount falling in a range of 0.5 g/L to 30 g/L of the sporulation broth.

5. The method of claim 4, wherein the starch is provided in an amount falling a range of 2 g/L to 5 g/L of the sporulation broth.

6. The method of claim 1, wherein the sporulation broth of the first liquid culture and the additional sporulation broth of the second liquid culture have the same composition.

7. The method of claim 1, wherein a volume of the first liquid culture is in the range of 20 mL-75 mL.

8. The method of claim 1, wherein a volume of the second liquid culture is in the range of 700 mL-3000 mL.

9. The method of claim 1, wherein a volume of the second liquid culture is in the range of 700 mL-2400 mL.

10. The method of claim 1, wherein a volume of the second liquid culture is in the range of 700 mL-1600 mL.

11. The method of claim 1, wherein a volume of the second liquid culture is in the range of 750 mL-850 mL.

12. The method of claim 1, wherein a ratio of a volume of the second liquid culture to a volume of the first culture is in the range of 10:1-120:1.

13. The method of claim 1, wherein a ratio of the volume of a second liquid culture to the volume of a first culture is in the range of 10:1-80:1.

14. The method of claim 1, wherein a ratio of the volume of a second liquid culture to a volume of the first culture is in the range of 10:1-45:1.

15. The method of claim 1, wherein the incubation of the first liquid culture is conducted for a period of time falling in a range of 2 hours-8 hours.

16. The method of claim 1, wherein the incubation of the second liquid culture is conducted for a period of time falling in a range of 12 hours-48 hours.

* * * * *